United States Patent [19]

Franklin

[11] 4,139,730
[45] Feb. 13, 1979

[54] METHOD OF TESTING HUMAN AUDITORY RESPONSES

[76] Inventor: Barbara Franklin, 3580 Louis Rd., Palo Alto, Calif. 94303

[21] Appl. No.: 823,278

[22] Filed: Aug. 10, 1977

[51] Int. Cl.² .............................................. A61B 5/12
[52] U.S. Cl. .................................... 179/1 N; 128/2 Z
[58] Field of Search ........................ 179/1 N; 128/2 Z

[56] References Cited
U.S. PATENT DOCUMENTS

| | | | |
|---|---|---|---|
| 1,586,952 | 6/1926 | Knudsen et al. .................... | 179/1 N |
| 1,750,960 | 3/1930 | Langenbeck et al. ............... | 179/1 N |
| 3,784,750 | 1/1974 | Stearns et al. ....................... | 179/1 N |
| 3,848,091 | 11/1974 | Stearns et al. ....................... | 179/1 N |

*Primary Examiner*—George G. Stellar
*Attorney, Agent, or Firm*—Richard K. Franklin

[57] ABSTRACT

An audiometric testing technique uses filtered speech bands which are attenuated and presented to a subject at different intensity levels. By producing a plurality of frequency bands of the speech pattern at different frequencies and presenting each of the frequency bands at a different intensity level, an audiogram is obtained.

2 Claims, 2 Drawing Figures

METHOD OF TESTING HUMAN AUDITORY RESPONSES

BACKGROUND OF THE INVENTION

1. Field of the Invention

This invention relates to a method of testing the auditory responses in human beings.

2. Prior Art

Testing for auditory response in humans is well known, and modern technology has provided sophisticated instruments designed to produce measures of the auditory response (audiograms) in an accurate and reproducible manner. A number of manufacturers in the United States and other countries make such devices for use in clinics, laboratories, and enterprises engaged in the sale of amplification devices such as hearing aids.

Prior art audiometric devices utilize a pure tone, i.e., a signal of a single, selected frequency at a number of predetermined frequency levels to test the response of the subject at each such frequency level through a range of signal intensity. The auditory response of the subject is then presented as the familiar audiogram.

The pure tone or signal at a predetermined frequency offers the advantage of being mechanically or electronically generated with identical reproduction, thus permitting a theoretical uniformity of test results from one testing center to another testing center and from one audiologist to another audiologist, and from one instrument to another instrument.

However, while the use of single-tone testing permits uniformity of tests, the test results are not always uniform or satisfactory. This has proven to be particularly true in the determination of proper amplification aids for individuals with impaired hearing. It has also been observed that there are anomalies in response to pure tones, particularly among infants and very young children with limited grasp of the testing situation. It has been observed, particularly with infants and young children, that use of familiar words and phonemes permits obtaining an audiogram that is different in significant respects from that obtained with pure tone signals. Moreover, the use of familiar words and phonemes provides test results which reflect more accurately the frequencies at which amplification assistance is desired and the extent of such assistance.

Northern and Downs, in *Hearing in Children*, Williams & Wilkins Co., Baltimore, Md. (1974), present results comparing thresholds for speech and a warbled pure tone and conclude that speech produces a significantly lower threshold than pure tones for tested individuals at varying age levels. Eisenberg, in *Auditory Competence in Early Life, the Roots of Communicative Behavior*, University Park Press, Baltimore, Md. (1976), cites numerous studies which have shown that speech is the most effective auditory stimulus for obtaining a response in newborns, infants and young children. Condon and Sander present findings on neonate respnse to speech in "Neonate movement is synchronized with adult speech: Interactional participation and language acquisition," *Science*, 183:99–101, 1974.

Thus, while there is a general recognition that speech is a more effective elicitor of human response than pure tone for infants, young children, and hard-to-test subjects, speech has not been used for auditory testing because of the inability to obtain quantitative information corresponding to an audiogram.

SUMMARY AND DESCRIPTION OF THE INVENTION

Figures 1, 2:
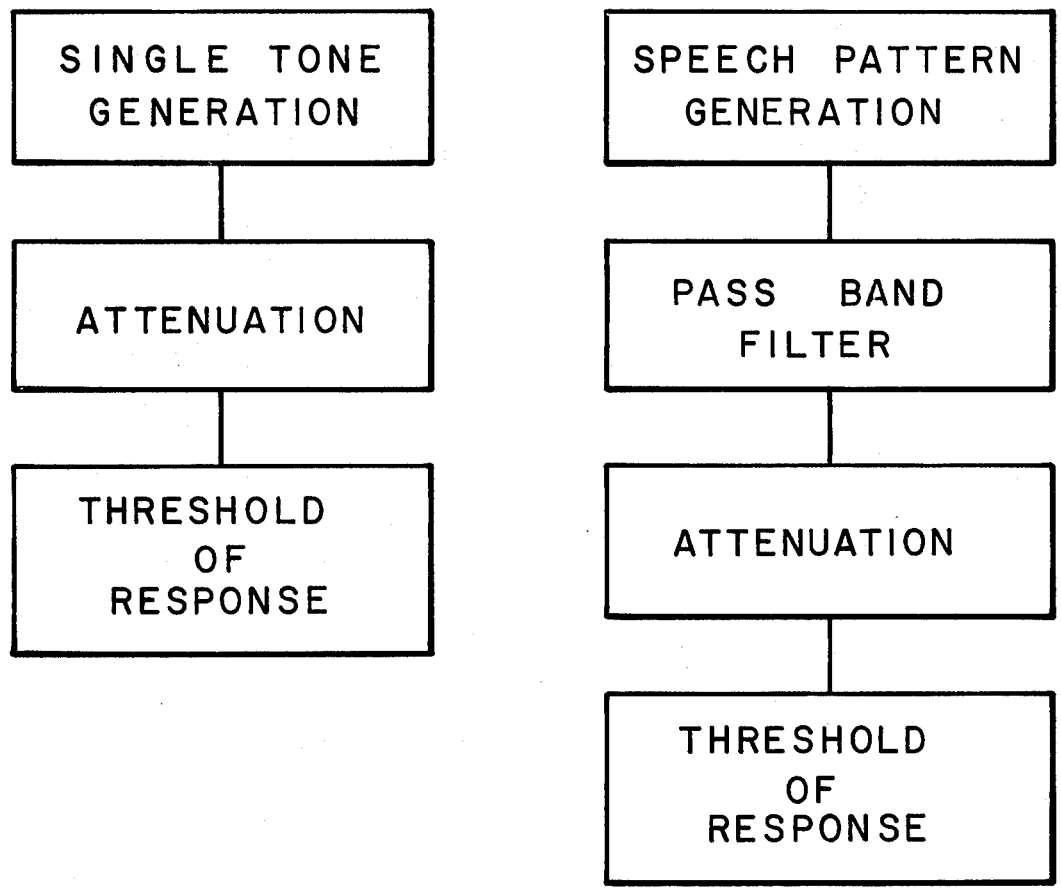
FIG. 1 is a simplified flow diagram of the prior-art method of testing for auditory response using a single tone.
FIG. 2 is a simplified flow diagram of the method of testing for auditory response using a filtered speech pattern in accordance with the present invention.

In accordance with the present invention, an improved audiometric testing technique uses filtered speech bands which can be used either as an alternative or a supplement to pure-tone testing. A human speech pattern is generated and filtered to produce a limited frequency band of the speech pattern. The limited frequency speech pattern band is attenuated and applied to a subject at different intensity levels. By producing a plurality of frequency bands of the speech pattern at different frequencies and presenting each of the frequency bands at different intensity levels to a subject, a useful audiogram is obtained. This method of testing for auditory response is readily implemented with conventional electronic equipment including recording instruments and electronic filtering equipment.

In one embodiment of the process, the phrase "Ah, ah, baby, clap, clap, clap, clap," spoken by a female, has been used as the speech pattern in actual application of the method of testing for auditory response in accordance with the present invention. This speech pattern was filtered using various low-frequency cutoff points of 250, 500, 1000, 2000 and 4000 Hz with serial high-pass filters which provided approximately 60 dB/octave signal drop. The results for three individual subjects are given below:

| | SUBJECT #1 RIGHT EAR | | | | |
|---|---|---|---|---|---|
| STIMULUS | 250 Hz | 500 | 1000 | 2000 | 4000 |
| PURE TONE | 60 dB | 85 | 85 | 85 | 80 |
| SPEECH BAND | 60 | 75 | 75 | 75 | 75 |
| | LEFT EAR | | | | |
| STIMULUS | 250 Hz | 500 | 1000 | 2000 | 4000 |
| PURE TONE | 85 dB | 85 | 80 | 75 | 70 |
| SPEECH BAND | 70 | 70 | 70 | 70 | 65 |
| | SUBJECT #2 RIGHT EAR | | | | |
| STIMULUS | 250 Hz | 500 | 1000 | 2000 | 4000 |
| PURE TONE | 60 dB | 85 | 95 | 95 | 85 |
| SPEECH BAND | 65 | 80 | 85 | 85 | 85 |
| | LEFT EAR | | | | |
| STIMULUS | 250 Hz | 500 | 1000 | 2000 | 4000 |
| PURE TONE | 65 dB | 75 | 95 | 90 | 80 |
| SPEECH BAND | 65 | 70 | 80 | 80 | 75 |
| | SUBJECT #3 RIGHT EAR | | | | |
| STIMULUS | 250 Hz | 500 | 1000 | 2000 | 4000 |
| PURE TONE | 80 dB | 85 | 100 | 105 | 105 |
| SPEECH BAND | 75 | 75 | 85 | 90 | 85 |
| | LEFT EAR | | | | |
| STIMULUS | 250 Hz | 500 | 1000 | 2000 | 4000 |
| PURE TONE | 75 dB | 100 | 105 | 105 | 110 |
| SPEECH BAND | 80 dB | 90 | 95 | 95 | 95 |

It can be seen that the speech-band thresholds for easy-to-test subjects tend to be slightly lower than the pure-tone thresholds. In fact, the method of testing for auditory response in accordance with the present invention has been successfully employed for obtaining audiograms for many hard-to-test, low functioning, deaf/blind and/or retarded children for whom audiograms could not be obtained using conventional pure-tone audiometric procedures.

In another embodiment of the invention which has proved effective in testing previously untestable children, five test bands were employed with each band centered at the same test frequency as on a standard audiometer with the acoustic energy in each of the five bands matched as closely as possible. The test bands were defined as follows:

| Center Frequency | Band Width |
| --- | --- |
| 250 Hz | 125–375 Hz |
| 500 Hz | 250–750 Hz |
| 1000 Hz | 750–1500 Hz |
| 2000 Hz | 1500–2500 Hz |
| 4000 Hz | 3000–5000 Hz |

While the invention has been defined with reference to specific embodiments and applications, it will be appreciated by those skilled in the art that the invention is not so limited, and many modifications and amplifications may be made by those skilled in the art without departing from the spirit and scope of the invention as defined by the appended claims.

I claim:

1. Method of testing for auditory response, especially useful in testing infants and hard-to-test subjects comprising the steps of:
   a. generating a speech pattern
   b. filtering said speech pattern to produce a plurality of limited-frequency bands of said speech pattern so that each said band is centered at a unique selected frequency different from the frequencies at which the other bands are centered, each selected frequency being fixed, once selected, and each said band having approximately equal accoustic energy,
   c. presenting said limited frequency bands, sequentially, at different intensity levels to a subject, and
   d. identifying the threshhold level of hearing said speech pattern for each of of limited frequency bands.

2. A method of testing for auditory response as defined by claim 1 wherein said frequency bands are defined by the following center frequencies and band widths:

| Center Frequency | Band Width |
| --- | --- |
| 250 Hz | 125–375 Hz |
| 500 | 250–750 |
| 1000 | 750–1500 |
| 2000 | 1500–2500 |
| 4000 | 3000–5000 |

* * * * *